United States Patent [19]

Beacon et al.

[11] Patent Number: 4,950,293
[45] Date of Patent: Aug. 21, 1990

[54] PROSTHETIC LIGAMENTARY DEVICE

[76] Inventors: Jonathan P. Beacon, Sewell Manor, Sewell, Dunstable, Bedfordshire; Raymond C. Wadey, 18 Great Woods, Edington, Westbury, Wiltshire, both of United Kingdom

[21] Appl. No.: 270,720

[22] Filed: Nov. 14, 1988

[30] Foreign Application Priority Data

Sep. 2, 1988 [GB] United Kingdom ............... 8820766

[51] Int. Cl.$^5$ .............................................. A61F 2/08
[52] U.S. Cl. ..................................................... 623/13
[58] Field of Search ............................ 623/13, 14, 20; 128/334 R

[56] References Cited

U.S. PATENT DOCUMENTS 4,795,466 1/1989 Stuhmer et al. ...................... 623/13

FOREIGN PATENT DOCUMENTS 0249346 12/1987 European Pat. Off. ............. 623/13

Primary Examiner—Ronald L. Frinks
Attorney, Agent, or Firm—Brian J. Coyne

[57] ABSTRACT

A prosthetic ligamentary device consists of one or two longitudinal elements of relatively inelastic material and an element of relatively elastic material. When the longitudinal elment (s) is or are subjected longitudinally to an anatomical tensile force, it or they extend (s) to a limited degree by transversely compressing the relatively elastic element, until the force is incapable of compressing the latter element further, whereupon the device becomes inextensible by the force. Two devices can be combined to form a cruciate ligament prosthesis for a knee joint.

20 Claims, 5 Drawing Sheets

PROSTHETIC LIGAMENTARY DEVICE

BACKGROUND OF THE INVENTION

1. Field of the Invention

This invention relates to a prosthetic ligamentary device.

2. Description of the Prior Art

From an anatomical point of view, it is desirable for an artificial ligament, during extension, to have elasticity followed by ridigity.

A prosthetic ligamentary device has been suggested consisting of a relatively inelastic cord attached at one end to one end of a helical tension spring. In its application to a knee joint, the cord is anchored at its other end to the tibia and extends at its one end into a hole drilled through the condyle of the femur and the other end of the spring is anchored to the femur outside the hole.

In use of the joint, the one end of the cord must move longitudinally in the hole, but this is disadvantageous, because the one end of the cord should preferably be immobile in the hole, particularly to allow growth of natural material into the cord if the latter is foraminous.

U.S. Pat. No. 4255820 discloses an artificial ligament which is tubular in overall configuration with flared ends, which have a graduated pore density to permit controlled hard and soft tissue ingrowth, and a central portion which prevents tissue ingrowth. The central section of the ligament is formed so as to be elastic along its longitudinal axis to permit the needed elasticity in use, having an elongation factor of between 4 to 6% of its length. Inserted within the central section is a cylindrical core of DACRON (a polyester formed by reaction between terephthalic acid and ethylene glycol), or cross-linked or vulcanized rubber, or high-density polyethylene. The core is effective to maintain the tubular shape of the ligament and to provide strain relief throughout the central section.

SUMMARY OF THE INVENTION

According to one aspect of the present invention, there is provided a prosthetic ligamentary device comprising a first means which is relatively inelastic longitudinally of the device, and a second means which is relatively elastic transversely of the device, said first means, at said second means and in one longitudinal direction of said first means, diverging outwardly and then converging inwardly, so that the subjection of the first means to an anatomical tensile force increases the length of the first means against the action of the second means to a limited degree and thereupon said first means becomes virtually inextensible by said force.

Owing to the invention, it is possible to arrange for the second means, and thus the extension of the device, to be sited at the free zone of the device, whereby both ends of the ligament can be immobile, and yet for the device, during extension, to have elasticity followed by rigidity.

Advantageously, the first means diverges and converges as aforesaid about the second means and the latter is compressed by the extending of the first means so that the first means is extended until the second means can be compressed no further by the tensile force.

According to another aspect of the present invention, there is provided a cruciate ligament prosthesis, comprising first and second prosthetic ligamentary devices a section of at least one of which, when subjected longitudinally to an anatomical tensile force, increases in length to a limited degree and thereupon becomes virtually inextensible.

The cruciate ligament prosthesis may comprise only three arms radiating from a region at which the arms are interconnected, one of the three arms being virtually inextensible when subjected longitudinally to an anatomical tensile force, and at least one of the other two arms comprising a section which, when subjected longitudinally to an anatomical tensile force, increases in length to a limited degree and thereupon becomes virtually inextensible.

Such Y-form prosthesis is advantageous over an X-form cruciate ligament prosthesis in certain circumstances, for example where the X-form prosthesis' requirement for two drilled anchorage holes in the tibia may weaken the tibia excessively so that use of a single drilled hole in the tibia required with the Y-form prosthesis reduces the weakening, or where there is insufficient room to anchor two arms, for example because the bone is too small, or there is a plate, or part of a prosthetic joint, or soft tissue where one or both of the anchorages is or are required for the X-form prosthesis.

In a particularly advantageous embodiment of this Y-form prosthesis, the prosthesis includes two hollow longitudinal elements of relatively inelastic material, the two elements extending one within the other to form the aforesaid one of the three arms.

In cases where the cruciate ligament prosthesis comprises first, second and third (and possibly fourth) arms radiating from a region at which the arms are interconnected, the first (and fourth) arm(s) being virtually inextensible when subjected longitudinally to an anatomical tensile force, and the second and third arms each comprising a section which, when subjected longitudinally to an anatomical tensile force, increases in length to a limited degree and thereupon becomes virtually inextensible, a single open-mesh sleeve may encircle these sections, be fastened at the ends thereof to the second and third arms at locations beyond the sections and be of material which is extensible with said sections. However, it is preferable for individual open-mesh sleeves to encircle the respective sections, instead of the single sleeve encircling both sections, because individual sleeves give greater flexibility in use of the prosthesis, in particular where a greater angle is required in situ between the second and third arms than would be allowed for by the single sleeve.

According to a further aspect of the present invention, there is provided a method of inserting a prosthetic ligamentary device at a joint between first and second bones, comprising:

providing a prosthetic ligamentary device a section of which, when subjected longitudinally to an anatomical tensile force, increases in length to a limited degree and thereupon becomes virtually inextensible by said force, and anchoring respective end zones of said device to the respective bones, with said section located between said bones.

BRIEF DESCRIPTION OF THE DRAWINGS

In order that the invention may be clearly understood and readily carried into effect, reference will now be made, by way of example, to the accompanying drawings, in which.

DESCRIPTION OF THE PREFERRED EMBODIMENTS

Figure 1:
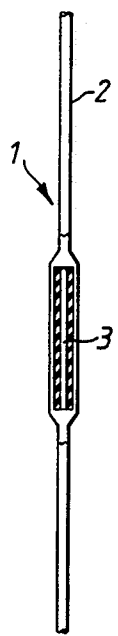
FIG. 1 shows a diagrammatic sectional view of a prosthetic ligamentary device.
Figure 2:
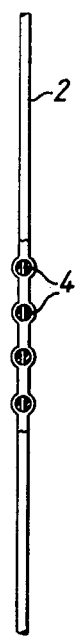
FIG. 2 is diagrammatic section view of a modified version of the device.

Referring to FIG. 1, the prosthetic ligamentary device 1 consists of a hollow longitudinal element 2 of a relatively inelastic material and containing a hollow element 3 of relatively elastic material. The element 2 may be a cross-woven cord of polyester, whilst the element 3 may be a tube of silicone rubber co-axial with the element 2. When the element 2 is subjected longitudinally to an anatomical tensile force it extends to a limited degree by transversely compressing the tube 3, until the force is incapable of compressing the tube 3 further, whereupon the device 1 becomes inextensible by the force. By appropriate selection of the length and/or diameter of the tube 3, the degree of maximum extension of the device 1 can be preset. In the version shown in FIG. 2, the hollow cord 2 contains spherical rubber beads 4 instead of the tube 3. Similarly, by appropriate selection of the number and diameter of the beads 4, the degree of maximum extension of the device can be preset.

Figure 3:
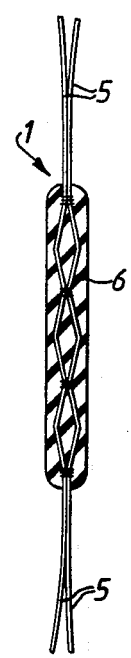
FIG. 3 shows a diagrammatic sectional view of another modified version of the device.

Referring to FIG. 3, there are two longitudinal elements 5 which zig-zag towards and away from each other in a silicone rubber body 6. By selecting the dimensions of the body 6 and/or the number and/or dimensions of the zig-zags therein, the degree of maximum extension of the device 1 can be preset. In manufacturing the version shown in FIG. 3, the two cords 5 are passed in the zig-zags around pegs, their nodal zones are stitched together, and then the silicone rubber body 6 is cast around the zig-zag areas.

Figure 4:
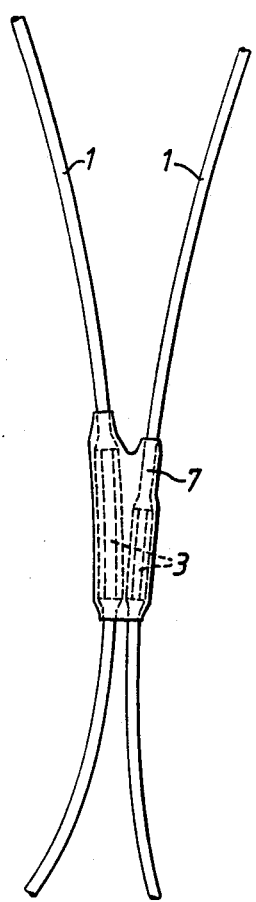
FIG. 4 shows a diagrammatic side elevation of a cruciate ligament prosthesis including two devices each according to the version of FIG. 1.

Referring to FIG. 4, the prosthesis includes two devices 1 encircled by a bicornuate sleeve 7 which is fastened at its ends to the devices 1 at locations beyond the tubes 3 and which is of open-mesh material which is extensible with the devices.

Because the tubes 3 are of differing lengths in the prosthesis shown in FIG. 4, differential maximum extension of the two devices 1 is achieved.

Figure 5:
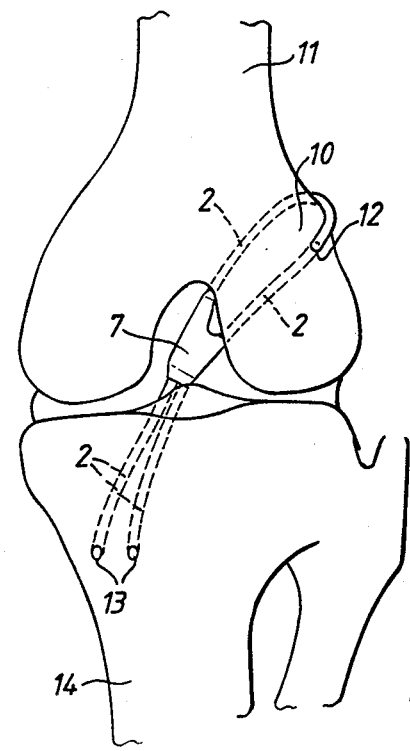
FIG. 5 is a front elevation of a left knee joint and shows the prosthesis of FIG. 4 as an anterior cruciate ligament prosthesis.
Figure 6:
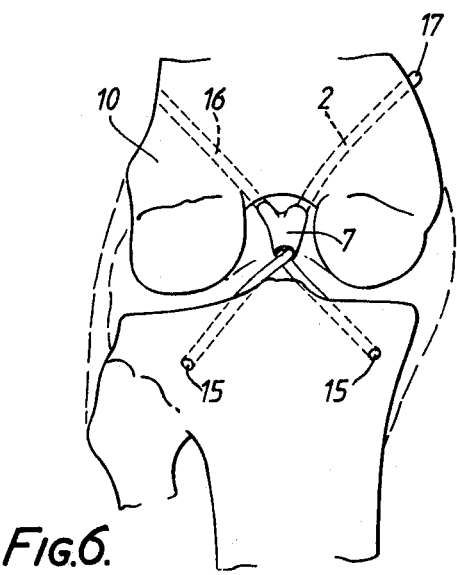
FIG. 6 is a rear elevation of a left knee joint and shows the prosthesis of FIG. 4 as a posterior cruciate ligament prosthesis.

It will be noted with reference to FIGS. 5 and 6 that the extending of the cords 2 and the sleeve 7 occurs within the free zone of the prosthesis within the joint. This is important because extending elsewhere would cause the cords to slide within the drilled holes, thus discouraging ingrowth of natural body material.

FIG. 5 shows an anterior application of the prosthesis of FIG. 4. The Figure shows that the proximal part of one of the cords 2 has been passed posteriorly around the condyle 10 of the femur 11 to be attached to the adjacent end of the proximal part of the other cord 2, which has been passed through a hole 12 drilled through the condyle 10. The central unit 3, 7 has been twisted into position, with the distal parts of both cords 2 passing through holes 13 drilled in the tibia 14 and being fixed thereto.

Figure 7:
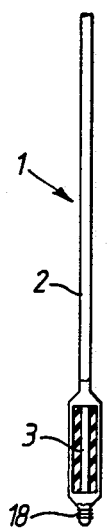
FIG. 7 is a diagrammatic sectional elevation of an acute reconstruction prosthetic ligamentary device.

Referring to FIG. 6, showing a posterior application of the prosthesis of FIG. 4, the distal parts of the cords 2 are passed through drilled holes 15 in the tibia 14 and are there fixed. The central unit 3, 7 of the prosthesis is again in a twisted condition. This time, while the proximal part of one of the cords 2 is passed through a drilled hole 16 in the condyle 10 and there fixed, the proximal part of the other cord 2 is passed around the front of the condyle and is fixed at the location 17.

Where an acute reconstruction of a ligament is required, the device may be of the form shown in FIG. 7, in which the cord 2 terminates just beyond one end of the tube 3 and is there provided with a fine cord whipping 18, with the end of the cord being heat-sealed to prevent fraying. The purpose of the fine cord whipping, which may be of polyester cotton, is to provide a sewing-in location for sutures to connect the device 1 to the damaged pole of the actual ligament.

Figure 8:
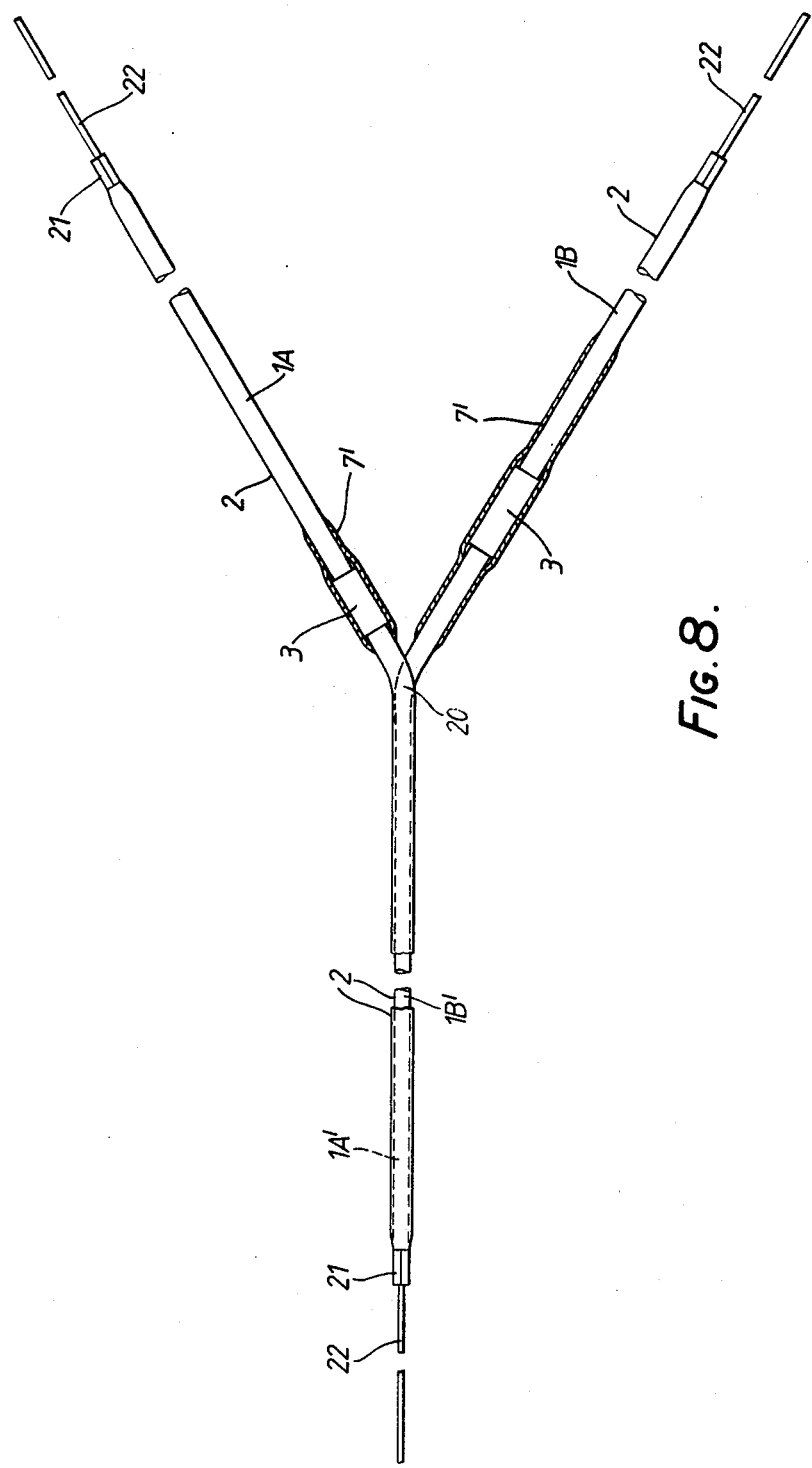
FIG. 8 shows a diagrammatic partly-sectional view of a modified version of the cruciate ligament prosthesis.

Referring to FIG. 8, the prosthesis shown comprises two prosthetic ligamentary devices 1A and 1B of which a part 1B' of the device 1B extends within a part 1A' of the device 1A, the hollow elements 3 of relatively elastic material being again disposed within the cords 2 but beyond the parts 1A' and 1B'. At the location 20 where the device 1B enters a small aperture in the wall of the cord 2 of the device 1A, the cords 2 are heat-sealed together. Thus, the prosthesis is of a Y-form with the three arms thereof radiating from the location 20. The outer ends of the three arms are crimped at 21 to respective relatively thin leaders 22 which are of polyester cord and which facilitate threading of the relatively thick cords 2 into the bores in the bones. In the regions of the respective tubes 3, the devices 1A' and 1B' are encircled by respective sleeves 7' which are fastened at their respective ends to the respective devices 1A and 1B at locations beyond their tubes 3 and which are of open-mesh material which is extensible with the devices. An advantage of having the sleeves 7' of open-mesh material is that the interstices thereby provided promote ingrowth of natural body material.

Figure 9:
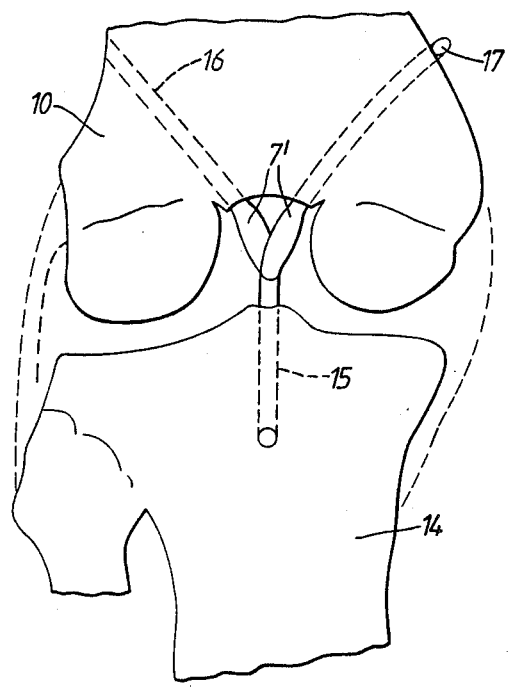
FIG. 9 is a rear elevation of a left knee joint and showing the prosthesis of FIG. 8 inserted.

Referring to FIG. 9, the double-cord arm is passed through a single drilled hole 15 in the tibia 14 and is there fixed. The central parts 3, 7' of the prosthesis are again in a twisted condition. Whilst the proximal part of the cord 2 of the device 1A is passed through a drilled hole 16 in the condyle 10 and there fixed, the proximal part of the other cord 2 is passed around the front of the condyle and is fixed at the location 17.

Although the Y-form prosthesis shown in FIG. 8 is described as inserted posteriorly with reference to FIG. 9, it is also suitable for anterior cruciate replacement.

Figure 10:
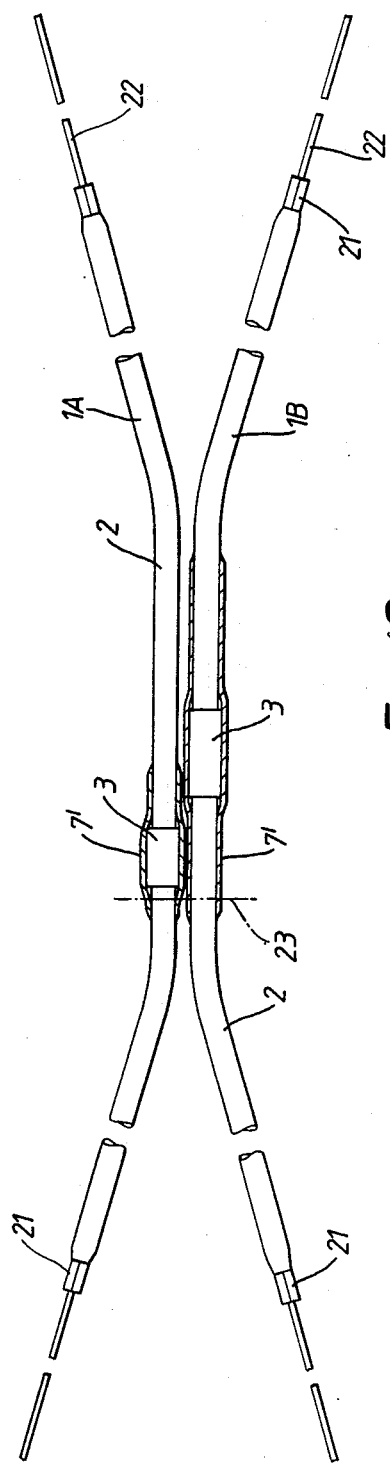
FIG. 10 shows a diagrammatic partly-sectional view of another modified version of the cruciate ligament prosthesis.

Referring to FIG. 10, the prosthesis shown is intended for use as an anterior cruciate ligament prosthesis and comprises two prosthetic ligamentary devices 1A and 1B, the hollow elements 3 of relatively elastic material being again disposed within the cords 2. The outer ends of the cords 2 are crimped at 21 to respective relatively thin leaders 22 of polyester cord. In the regions of the respective elements 3, the devices 1A and 1B are encircled by respective sleeves 7' which are fastened at their respective ends to the respective devices 1A and 1B at locations beyond their elements 3 and which are of extensible, open-mesh material. In the distal end zones of the sleeves 7', the devices 1A and 1B are bound together, for example by sewing, as indicated at 23. Thus, the prosthesis is of an H- or X-form with the four arms thereof radiating from the location 23.

The various materials of the various embodiments described with reference to the drawings may be totally biodegradable, partially biodegradable, or non-biodegradable.

An advantage of having the cord 2 and the sleeves 7 and 7' of woven material is that the interstices thereby provided promote ingrowth of natural body material.

The device 1 is deliberately implanted in a condition under tension for all positions of the knee and so is under continual tension in situ, owing to the relatively elastic element 3, and this predisposes towards the ingrowth of new living ligament material, with the intention of eventual production of a new biological ligament.

We claim:

1. A prosthetic ligamentary device comprising a first means which is relatively inelastic longitudinally of the device, and a second means which is relatively elastic transversely of the device, said first means, at said second means and in one longitudinal direction of said first means, diverging outwardly and then converging inwardly, so that the subjection of the first means to an anatomical tensile force increases the length of the first means against the action of the second means to a limited degree and thereupon said first means becomes virtually inextensible by said force.

2. A device according to claim 1, wherein said first means diverges and converges as aforesaid about said second means and the latter is compressed by the extending of said first means, so that said first means is extensible until said second means can be substantially compressed no further by said tensile force.

3. A device according to claim 2, wherein said first means comprises a hollow longitudinal element of relatively inelastic material and said second means comprises a hollow element of relatively elastic material and contained in said hollow longitudinal element.

4. A device according to claim 3, wherein said hollow longitudinal element comprises a cross-woven cord.

5. A device according to claim 3, wherein said hollow element is a tube.

6. A device according to claim 2, wherein said second means comprises beads.

7. A device according to claim 1, wherein said second means comprises a compact body and said first means comprises first and second longitudinal elements which extend in said body in a manner in which they zig-zag towards and away from each other.

8. A device according to claim 1, wherein said second means is substantially encircled by an open-mesh sleeve disposed exteriorly of said first means and said second means.

9. A device according to claim 8, wherein said open-mesh sleeve is fastened at its ends to said first means at respective locations beyond said second means.

10. A device according to claim 1, wherein said first means terminates just beyond one end of said second means and at that termination zone has means facilitating sewing-in of a suture.

11. A cruciate ligament prosthesis, comprising first and second prosthetic ligamentary devices a section of at least one of which comprises relatively inelastic material displaceable between a longitudinally extensible condition and a longitudinally inextensible condition and linked with relatively elastic material displaceable between a relatively unstressed condition and a relatively stressed condition, and thereby that section, when in an initial condition in which said relatively inelastic material is in said longitudinally extensible condition and said relatively elastic material is in said relatively unstressed condition and then subjected longitudinally to an anatomical tensile force, increases in length to a limited degree and thereupon becomes virtually inextensible by said force and, when in its virtually inextensible condition and then relieved of said force, restores itself promptly to said initial condition.

12. A prosthesis according to claim 11, wherein said first and second prosthetic ligamentary devices form only three arms radiating from a region at which the arms are interconnected, one of the three arms being virtually inextensible when subjected longitudinally to an anatomical tensile force, and at least one of the other arms comprising said section(s).

13. A prosthesis according to claim 12, wherein said first and second prosthetic ligamentary devices comprise respective first and second hollow longitudinal elements which are of said relatively inelastic material and which extend one within the other to form said one of the three arms.

14. A prosthesis according to claim 11, wherein said first and second prosthetic ligamentary devices form first, second and third arms radiating from a region at which the arms are interconnected, said first arm being virtually inextensible when subjected longitudinally to an anatomical tensile force and the other arms comprising said sections.

15. A prosthesis according to claim 14, wherein said first and second prosthetic ligamentary devices form said first, said second, said third, and fourth arms radiating from said region, said fourth arm being virtually inextensible when subjected longitudinally to an anatomical tensile force.

16. A prosthesis according to claim 11, wherein said section(s) is/are encircled by a single open-mesh sleeve.

17. A prosthesis according to claim 16, wherein said sleeve is fastened at the ends thereof to the devices at locations beyond said sections and is of material which is extensible with said sections.

18. A prosthesis according to claim 11, wherein said sections are encircled by respective open-mesh sleeves.

19. A prosthesis according to claim 18, wherein said sleeves are fastened at the ends thereof to the devices at locations beyond said sections and are of material which is extensible with said sections.

20. A method of inserting a prosthetic ligamentary device at a joint between first and second bones, comprising:
providing a prosthetic ligamentary device a section of which comprises relatively inelastic material displaceable between a longitudinally extensible condition and a longitudinally inextensible condition and linked with relatively elastic material displaceable between a relatively unstressed condition and a relatively stressed condition, and thereby that section, when in an initial condition in which said relatively inelastic material is in said longitudinally extensible condition and said relatively elastic material is in said relatively unstressed condition and then subjected longitudinally to an anatomical tensile force, increases in length to a limited degree and thereupon becomes virtually inextensible by said force and, when in its virtually inextensible condition and then relieved of said force, restores itself promptly to said initial condition, and anchoring respective end zones of said device to the respective bones, with said section located between said bones.

* * * * *